(12) United States Patent
Hough et al.

(10) Patent No.: US 8,775,205 B2
(45) Date of Patent: Jul. 8, 2014

(54) IMAGING DEVICE INFORMATION SYSTEM AND METHOD

(75) Inventors: Thomas W. B. Hough, Mississauga (CA); William A. Brodie, Burlington (CA); Lynn Kain, Burlington (CA); C. Blake Heald, Mississauga (CA); Steven Schiorke, Mississauga (CA); Christopher A. Fraser, Burlington (CA); Gurmukh Tej Dhillon, Ottawa (CA)

(73) Assignee: True North Consulting & Associates Inc., Mississauga, ON (CA)

( * ) Notice: Subject to any disclaimer, the term of this patent is extended or adjusted under 35 U.S.C. 154(b) by 0 days.

(21) Appl. No.: 13/806,943

(22) PCT Filed: Jun. 29, 2010

(86) PCT No.: PCT/CA2010/001005
§ 371 (c)(1),
(2), (4) Date: Mar. 13, 2013

(87) PCT Pub. No.: WO2012/000073
PCT Pub. Date: Jan. 5, 2012

(65) Prior Publication Data
US 2013/0173308 A1    Jul. 4, 2013

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| | | | |
|---|---|---|---|
| 7,170,621 B2 | 1/2007 | Aonuma | |
| 7,716,277 B2 | 5/2010 | Yamatake | |
| 2002/0152296 A1 | 10/2002 | Baker | |
| 2006/0031095 A1* | 2/2006 | Barth et al. | 705/2 |
| 2006/0242148 A1* | 10/2006 | Rothpearl et al. | 707/7 |

(Continued)

FOREIGN PATENT DOCUMENTS

EP    1338129 B1  *  11/2006

OTHER PUBLICATIONS

Boochevar, Stephen S., "HIS/RIS/PACS Integration: Getting to the Gold Standard," May/Jun. 2004, Radiology Management.*

(Continued)

*Primary Examiner* — Elaine Gort
*Assistant Examiner* — John Go
(74) *Attorney, Agent, or Firm* — Kagan Binder, PLLC

(57) ABSTRACT

A system and method for analyzing the utilization of diagnostic imaging modality devices by receiving and combining patient information from a radiology information system and image series information of patients from diagnostic imaging modality devices. The system may produce facility reports analyzing temporal utilization of the diagnostic imaging modality devices. It may also query a picture archiving and communication system to identify changes made to the image series information and update the facility database to reflect changes that are identified. The radiology information system may use a standard protocol, such as HL7, that is different from and not interoperable with a standard protocol, such as DICOM, used by the diagnostic imaging modality devices and picture archiving and communication system. The system may produce facility-independent reports for multiple imaging facilities that may be combined into regional reports by a regional information system.

19 Claims, 10 Drawing Sheets

(56) References Cited

U.S. PATENT DOCUMENTS

| | | | |
|---|---|---|---|
| 2008/0103834 A1* | 5/2008 | Reiner | 705/3 |
| 2008/0140451 A1* | 6/2008 | Hedrick et al. | 705/3 |
| 2009/0099867 A1* | 4/2009 | Newman | 705/2 |
| 2009/0099876 A1* | 4/2009 | Whitman | 705/3 |
| 2009/0182575 A1* | 7/2009 | Warner et al. | 705/2 |
| 2009/0254375 A1* | 10/2009 | Martinez et al. | 705/3 |
| 2010/0052930 A1 | 3/2010 | Grigsby et al. | |

OTHER PUBLICATIONS

Kallman, Hans-Erik, "DICOM Metadata repository for technical information in digital medical images," 2009, Acta Oncologica, 48:285-288.*

* cited by examiner

| Master Exam Table Element | Source | Definition | Sample Data |
|---|---|---|---|
| idC3_MasterRecord | IMAP | A unique record ID generated when a record is inserted into the database | 123456 |
| InsertedDateTime | IMAP | The date the record was inserted - this never changes | 2010-04-04 12:32 |
| LastUpdated | IMAP | The date the most recent update for the record was received | 2010-04-04 12:32 |
| LastCopied | IMAP | No longer used. | 2010-04-04 12:32 |
| AccessionID | hospital, HL7 | The unique number assigned to the exam for identification between the Radiology Information System and the PACS | 1234567 |
| AccessionIDCreatedDateTime | IMAP | The date the Accession ID is created | 2010-04-04 12:32 |
| PatientID | hospital, HL7 | The unique Patient ID number as assigned by the Hospital Information System or regional or national patient identification registry. | HC123456 |
| PatientName | hospital, HL7 | Name of the patient | Smith, John |
| OrderEnteredBy | hospital, HL7 | The name of the person who registered the exam. | Jones, Mary |
| ExamCodeFlag | IMAP | A 1 or 0 indicator generated by IMAP to indicate if the exam code supplied by the hospital is in the Exam Dictionary or not. (Used to identify new codes) | 1 |
| ExamCode | hospital, HL7 | The unique exam code for the exam performed on the patient as per the Hospital Exam Code Dictionary. | 12345CT |
| ExamDescription | Exam Dictionary | The description of the exam code, as defined in the hospital exam dictionary as supplied to IMAP | CT Brain, without contrast |
| ExamModalityType | Exam Dictionary | The modality to which the exam belongs, as provided by the hospital's exam dictionary | CT |

FIG. 4a

| Master Exam Table Element | Source | Definition | Sample Data |
|---|---|---|---|
| ExamSite | Calculated from Pt Account number | Site name (or abbreviation) the patient is associated with | ABC |
| PatientAccountNumber | hospital, HL7 | A unique number the patient is assigned by the HIS or RIS for this patient's interaction for this visit within the hospital | AX123456 |
| PatientType | Calculated from Pt Account number | Usually an alphabetic code to classify the patient as OP, IP, ER (This is sometimes part of the Patient Account Number) | OP |
| PatientArrivalDateTime | hospital, HL7 | The time the patient arrives at the Diagnostic Imaging department for the first exam / procedure. (If different from the Logged time) | 2010-04-04 12:32 |
| PatientReleaseDateTime | hospital, HL7 | The time the patient is released from the Diagnostic Imaging department upon the completion of each of their exams. (If different from the Taken time) | 2010-04-04 12:32 |
| OrderStatus | hospital, HL7 | A code representing the order status. (Ordered, Taken, Reported, etc.) | T |
| ObservationDateTime | hospital, HL7 | The requested/scheduled date the exam is scheduled to occur as placed in the order entry system. | 2010-04-04 12:32 |
| LoggedDateTime | hospital, HL7 | The date and time the patient registers at the DI Reception Desk for the first exam. | 2010-04-04 12:32 |
| TakenDateTime | hospital, HL7 | The date and time the technologist enters into the RIS to document that the exam has been taken. | 2010-04-04 12:32 |
| DraftDateTime | hospital, HL7 | The date and time the exam has a draft report completed. | 2010-04-04 12:32 |
| ResultedDateTime | hospital, HL7 | The date and time the exam has the diagnostic report signed off. | 2010-04-04 12:32 |

FIG. 4b

| Master Exam Table Element | Source | Definition | Sample Data |
|---|---|---|---|
| DICOM_AETitle | DICOM message header | Unique ID of the device that produced the images for the specific accession number | CT1 |
| DICOM_StudyDateTime | DICOM message header | Date and time of the first image from the device that produced the images for the specific accession number | 2010-04-04 12:32 |
| DICOM_LastImageDateTime | DICOM message header | Date and time of the most recent image from the device that produced the images for the specific accession number | 2010-04-04 12:34 |
| DICOM_ExamDuration | IMAP | Calculation of the exam duration in seconds | 120 |
| OrderingPhysician | hospital, HL7 | The name of the physician who ordered the exam. | Doctor, Joe |
| TechnologistAssigned1 | hospital, HL7 | The name of the Technologist(s) assigned to complete the exam – up to four | Green, John |
| TechnologistAssigned2 | hospital, HL7 | The name of the Technologist(s) assigned to complete the exam – up to four | White, Mary |
| TechnologistAssigned3 | hospital, HL7 | The name of the Technologist(s) assigned to complete the exam – up to four | Black, Joe |
| TechnologistAssigned4 | hospital, HL7 | The name of the Technologist(s) assigned to complete the exam – up to four | Brown, Harry |
| RadiologistAssigned | hospital, HL7 | The name of the Radiologist assigned to interpret and report the exam. | Doe, John |
| ExamCount | hospital's Exam Dictionary | The count of the exams associated with the Exam Code as defined and mapped by the hospital's exam dictionary | 1 |
| WLU | hospital's Exam Dictionary | The count of Workload Units assigned to the exam as defined and mapped by the hospital's exam dictionary | 23 |
| CIHI_ExamCount | Exam Dictionary mappings | The CIHI value of exam count associated with the Exam Code, as mapped by TNC staff | 1 |

FIG. 4c

| Master Exam Table Element | Source | Definition | Sample Data |
|---|---|---|---|
| CIHI_WLU | Exam Dictionary mappings | The CIHI value of Workload Units associated with the Exam Code, as mapped by TNC staff | 20 |
| GOLD_ExamCount | Exam Dictionary mappings | A standard reference of Exam Count for each particular exam code created and mapped by TNC staff | 1 |
| GOLD_WLU | Exam Dictionary mappings | A standard reference of Workload Units for each particular exam code created and mapped by TNC staff | 20 |
| GOLD_PFee | Exam Dictionary OHIP mappings | A standard value of Professional Fees associated with each exam code created and mapped by TNC staff, and referenced to the OHIP Schedule of benefits | $45.45 |
| GOLD_TFee | Exam Dictionary OHIP mappings | A standard value of Technical Fees associated with each exam code created and mapped by TNC staff, and referenced to the OHIP Schedule of benefits | $5.65 |
| OHIP_PFee | Calculated from OHIP components | The total OHIP Professional Fees for each exam as defined by the hospital's exam dictionary OHIP code mappings | $45.45 |
| OHIP_TFee | Calculated from OHIP components | The total OHIP Technical Fees for each exam as defined by the hospital's exam dictionary OHIP code mappings | $5.65 |
| OHIP_GPFee | Exam Dictionary OHIP mappings | A component of the total OHIP Professional Fee | $0.00 |
| OHIP_ATFee | Exam Dictionary OHIP mappings | A component of the total OHIP Professional Fee | $0.00 |
| OHIP_SFee | Exam Dictionary OHIP mappings | A component of the total OHIP Professional Fee | $0.00 |
| OHIP_AFee | Exam Dictionary OHIP mappings | The OHIP Technical Fee for DI as defined in the OHIP Schedule of Benefits | $5.65 |
| OHIP_NonAFee | Exam Dictionary OHIP mappings | A component of the total OHIP Professional Fee | $45.45 |

FIG. 4d

| Field Name | Sample Data | Notes |
| --- | --- | --- |
| ID | 24532 | Datacenter generates its own ID, not sent |
| HospitalID | 2 | ID of the hospital to the DataCenter |
| ModalityTypeCode | US | Type of modality |
| Aetitle | US1 | The AeTitle of the machine whose stats are generated |
| StatDate | 21/03/2010 | The date of the data |
| ExamCount | 12 | Number of exams based on LastImageTime |
| TakenExamCount | 10 | Number of exams based on TakenDateTime |
| ResultedExamCount | 13 | Number of exams based on ResultedDateTime |
| GoldCodeExamCount | 12 | # of exams based on LastImageTime, using GoldCode |
| GoldCodeTakenExamCount | 10 | # of exams based on TakenDateTime, using GoldCode |
| GoldCodeResultedExamCount | 13 | # of exams based on ResultedDateTime, using GoldCode |
| Utilization | 43899 | Total utilization throughout the date, based on LastImageTime |
| WLU | 348 | Number of WLU generated using TakenDateTime and hospital's WLU tables |
| CIHIWLU | 330 | Number of WLU generated using TakenDateTime and CIHI's WLU tables |
| GoldCodeWLU | 324 | Number of WLU generated using TakenDateTime and GoldCode's WLU table |
| TFee | 125.5 | Total TFee accrued for the day, using ResultedDateTime and hospital's amounts |
| GOLD_TFee | 78 | Total Gold TFee accrued for the day, using ResultedDateTime and GoldCode's amounts |
| PFee | 82.55 | Total PFee accrued for the day, using ResultedDateTime and hospital's amounts |
| GOLD_PFee | 107.75 | Total PFee accrued for the day, using ResultedDateTime and GoldCode's amounts |
| GPFee | 0 | Total GPFee accrued for the day, using ResultedDateTime and hospital's amounts |
| ATFee | 125.5 | Total ATFee accrued for the day, using ResultedDateTime and hospital's amounts |
| SFee | 0 | Total SFee accrued for the day, using ResultedDateTime and hospital's amounts |
| AFee | 80.11 | Total AFee accrued for the day, using ResultedDateTime and hospital's amounts |
| NonAFee | 82.55 | Total NonAFee accrued for the day, using ResultedDateTime and hospital's amounts |
| UploadDateTime | 22/03/2010 | Date data was sent to the DataCenter |

FIG. 5

IMAGING DEVICE INFORMATION SYSTEM AND METHOD

FIELD OF THE INVENTION

The present invention relates to systems and methods for managing the use of imaging devices.

BACKGROUND OF THE INVENTION

A radiology information system (RIS) used in a hospital typically employs the Health Level 7 (HL7) international standard for messaging that defines a series of healthcare events, records and messages to support administrative, logistical, financial as well as clinical processes. HL7 is not designed to support the exchange of image data. HL7 messages are broadcast on internal and inter-hospital networks to indicate events such as the admission, discharge or transfer of a patient, or, for example, to record the fact that the results of a Diagnostic Imaging (DI) test have been recorded in the RIS. The HL7 data stored in the RIS may include fields such as patient ID, patient name, gender and address, date and time of admission, name of referring physician, name of radiologist, as well as test-specific information. For example, if a magnetic resonance (MR) study has been requested for a patient, then the HL7 data for that patient may indicate the procedure code for such a request, the requesting physician, imaging status and report status.

Diagnostic image data is typically handled by a picture archiving and communication system (PACS). PACS systems generally store and transmit data in accordance with the Digital Imaging and Communications in Medicine (DICOM) international standard. Imaging modalities, such as MR and other diagnostic imaging devices, generally communicate directly with the PACS over a network using DICOM. The function of the PACS is to maintain a database of diagnostic images taken on connected devices along with related information for image display and patient demographics.

In addition to the image data, the DICOM records include accession number, the start and end times of tests, demographic information such as patient identification information, and may include identification of the attending staff member(s).

Information must be transmitted between such RIS and PACS systems and DI modality devices, for example, in order to indicate which tests have been ordered on which patients, and report when image studies have been completed.

For example, after an MR test has been completed, the interpreting radiologist will render a medical opinion report on the images, which is stored the RIS and PACS in one of several possible different formats.

The lack of interoperability between HL7 and DICOM has been a longstanding problem as is the variability in the use and interpretation of these standards. Manual transfer of data is expensive and error-prone. There have been attempts to harmonize the standards using integration profiles (IP's) to achieve specific interoperability, which has been led by an organization known as IHE (integrating the healthcare enterprise) working group. Unfortunately, these have been of limited success and achieved only limited interoperability. Some automated approaches have been employed such as the use of a "broker" system or software to translate between the two protocols so that a RIS can communicate directly with a modality (such as MR) and/or PACS. However, such solutions are expensive, and are error-prone because of the varying interpretations and use of the standards.

After the modality and/or PACS information is made available to the RIS and incorporated into the RIS database, the RIS may then be able to produce reports relating to the use of the imaging modalities and use of staff. For example, the RIS may provide aggregated monthly reports on the total number of ultrasound tests completed, the total technical fees, professional fees and workload units claimed for each month. This may be accompanied with variances from the previous year and the current budget. Reports showing the total workload units on a modality by modality basis or other aggregated basis for a certain period are also typically produced four to six weeks after the period.

It may be very useful to compare such information across multiple hospitals so each hospital can identify efficiencies or deficiencies in its utilization of imaging modalities and take corrective action. Such comparisons are very difficult because the procedure (study) code dictionaries are not standardized and are used differently by different hospitals. The Canadian Institute for Health Information (CIHI) provides a set of standardized code guidelines for hospital workload units for every procedure completed in health care in Canada. However, hospitals vary from these guidelines. When CIHI suggests 12 workload units to complete a two view chest radiography study and the hospital consistently takes 18 workload units to complete the study, then the hospital will change its own procedural dictionary to 18 workload units. In addition, the combination of certain studies into a single exploding code for convenience varies from hospital to hospital depending on the radiologists' preferences for study grouping. This makes the standardization of study dictionaries more difficult.

SUMMARY OF THE INVENTION

The invention provides an imaging facility device information system for use in an imaging facility having a radiology information system, a picture archiving and communication system and a plurality of diagnostic imaging modality devices, all of the foregoing connected to a local network, the facility information system comprising:

a. a facility imaging modality analysis processor connected to the local network for receiving patient information from the radiology information system and for receiving image series information of patients from the diagnostic imaging modality devices; and b. a facility database in electronic communication with the facility imaging modality analysis processor, wherein the facility imaging modality analysis processor combines image series information of each patient with patient information for the corresponding patient into patient records in the facility database and produces facility reports from the patient records analyzing temporal utilization of the diagnostic imaging modality devices.

The facility imaging modality analysis processor may query the picture archiving and communication system to identify changes made to the image series information and the facility imaging modality analysis processor may update the facility database to reflect changes that are identified.

The facility imaging modality analysis processor may receive image series information using a standard imaging system protocol and receives patient information using a standard radiology information system protocol. The standard radiology information system protocol may be HL7 and the standard imaging system protocol may be DICOM.

The facility imaging modality analysis processor may allow authorized facility users to request facility reports using a web browser.

The invention also provides for a method for analyzing temporal utilization of diagnostic imaging modality devices comprising the steps of:
 a. receiving patient information from a radiology information system;
 b. receiving image series information of patients from the diagnostic imaging modality devices;
 c. combining image series information of each patient with patient information for the patient into patient records; and
 d. producing facility reports from the patient records analyzing temporal utilization of the diagnostic imaging modality devices.

The method may further comprise the steps of:
 e. querying a picture archiving and communication system to identify changes made to the image series information; and
 f. updating the facility database to reflect changes that are identified.

In the method the image series information may be received using a standard imaging system protocol and the patient information may be received using a standard radiology information system protocol. The standard radiology information system protocol may be HL7 and the standard imaging system protocol may be DICOM.

The method may further comprise the steps of analyzing the facility reports to identify an under-utilized diagnostic imaging modality device and increasing the number of imaging facility staff attending that diagnostic imaging modality device so that the temporal utilization of the under-utilized diagnostic imaging modality device is increased.

The method may further comprise the steps of analyzing the facility reports to determine that a diagnostic imaging modality device has a technical problem and having technicians repair the diagnostic imaging modality device.

The invention also provides for an imaging device regional information system comprising:
 a. at least two imaging facility device information systems connected to a wide area network, and
 b. a regional imaging modality analysis processor connected to the wide area network,
 wherein the imaging facility device information systems produce facility-independent exam record summaries that are transmitted to the regional imaging modality analysis processor and wherein the regional imaging modality analysis processor produces regional reports from the facility-independent exam record summaries comparing the temporal utilization of the diagnostic imaging modality devices between imaging facilities.

The regional imaging modality analysis processor may allow authorized regional users to request regional reports using a web browser.

The imaging facility device information systems may update the patient records in real-time and may send the exam record summaries to the regional imaging modality analysis processor in real-time or near real-time, and the regional imaging modality analysis processor may then produce regional reports in real-time or near real-time.

BRIEF DESCRIPTION OF THE DRAWINGS

FIGS. 4a-4d show an example of data that may be stored in a facility database.

FIG. 5 is an example of an exam record summary.

DETAILED DESCRIPTION OF THE INVENTION

Figure 1:
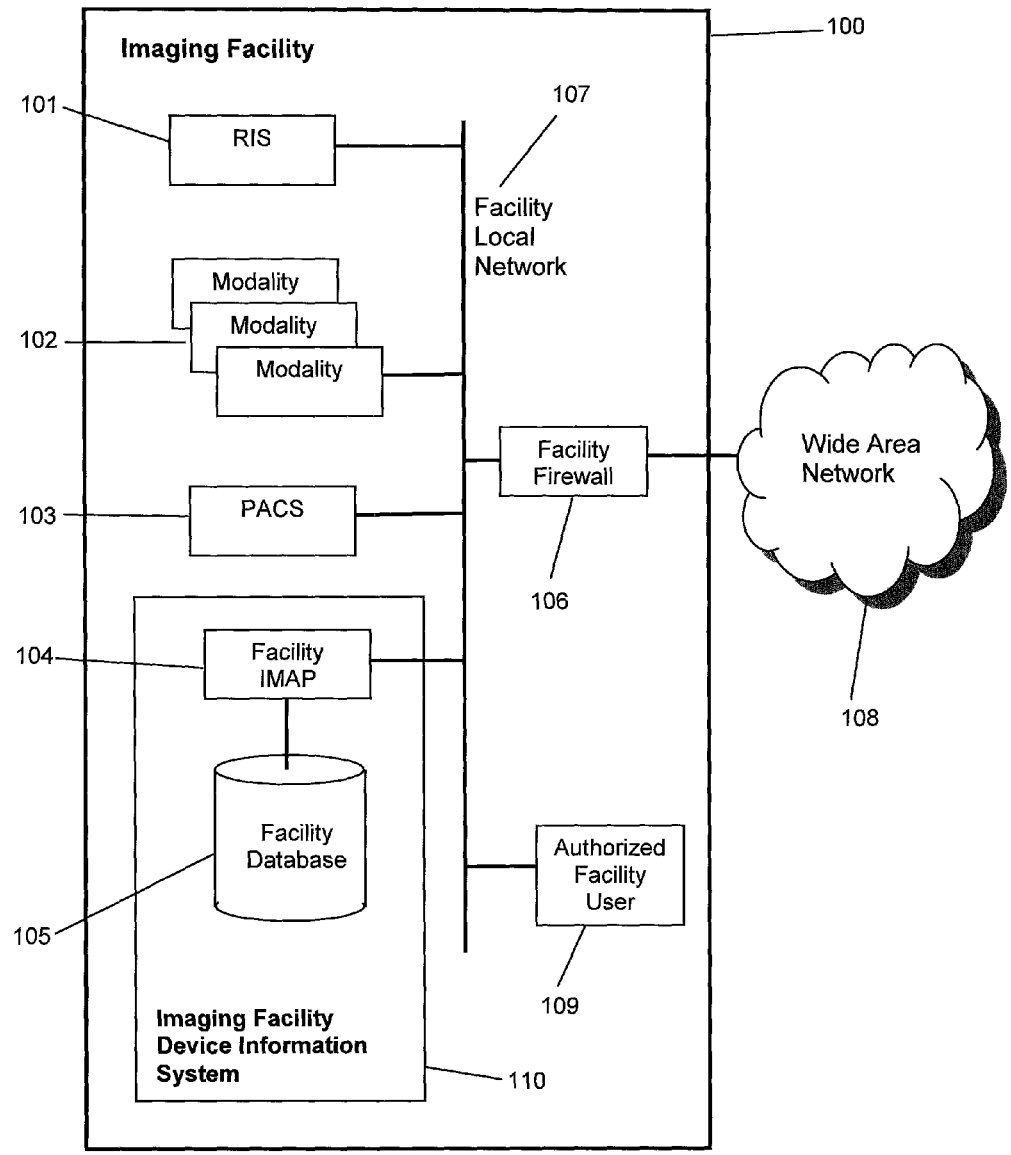
FIG. 1 is a diagram showing the invention and interoperating equipment within an imaging facility.

The system, in a preferred embodiment, which may be referred to as an imaging facility device information system 110, as shown in FIG. 1, consists of a facility imaging modality analysis processor (facility IMAP) 104 and a facility database 105, which is connected to and managed by the facility IMAP 104. The facility IMAP 104 is connected to a facility local network 107. The system is located at an imaging facility 100, such as a hospital, typically having a RIS 101, a PACS 103 and one or more modalities 102. Each modality 102 is a class of DI devices, such as computed tomography (CT), and includes at least one device of that modality, referred to as a DI modality device or a diagnostic imaging modality device. For example, a hospital may have one MR device, two CT devices and five Ultrasound (US) devices. The RIS 101, modalities 102, and PACS 103 are all connected to the facility local network 107. The imaging facility 100 may also have a facility firewall 106 that connects the facility local network 107 to a wide area network 108, such as the Internet. In addition to collecting data and populating the facility database 105, the facility IMAP 104 also produces facility reports based on the data in the facility database 105. Such facility reports reflect the real-time status of the DI modality devices, and may be requested via a GUI by an authorized facility user 109 on the facility local network 107.

Facility reports may also be generated showing statistics on an aggregated basis, such as for all devices of a DI modality 102.

The RIS 101 maintains patient information for each patient, such as a unique patient identifier, the patient's name, address and date of birth, the admitting physician's name and a list of all accession numbers for the patient along with the corresponding procedure numbers for each associated exam or group of exams that has been ordered for that patient. Each exam may include one or more studies using a particular imaging modality, each study having a unique procedural code. A study may include a number of image series, each of which is a series of one or more images of a patient acquired, or to be acquired, on a DI modality device, sequentially in time.

An image series complying with the DICOM standard for file transfer and sharing is composed of two segments. The first segment is the DICOM header, which consists of patient demographic information and a number of data fields identifying the technical specifications required to read the study images and present them in an appropriate arrangement, window and level of greyscale, including the time of first image capture, time of last image capture, and where to start to read the data set to display the images, and other technical factors. The second segment of the DICOM file is the binary image data that is the image series. This segment of the DICOM file can be very large as it can in some cases include thousands of images for a single image series.

The RIS 101 may employ a standard radiology information system protocol, such as HL7, for storing patient information and transmitting patient information on the facility local network 107. The RIS, using HL7, has a number of types of messages it can use to send information to other devices on the network. HL7 employs the technique of broadcasting messages across the network, which permits any device connected to the network to listen and use the data. Two such messages are named ORU and ORC, which are for the transfer of data. The types of data transferred may consist of messages containing information such as the patient ID number, patient number, gender, date of birth, referring physician, area the patient is being referred in the hospital from (inpatient, outpatient, emergency department), the type of study requested, the procedural code for the requested study, and the time and location of the study to be completed. A message may also be a confirmation that the study has been reported by a radiologist and is now available through the hospital information system (HIS) for viewing by other clinicians providing healthcare to the patient.

Within the facility IMAP 104 the information collected and put into the facility database 105 includes information such as PatientID, PatientName, OrderEnteredBy, PatientAccountNumber, ExamCode, AccessionID, PatientArrivalDateTime, PatientReleaseDateTime, OrderStatus, ObservationDateTime, LoggedDateTime, TakenDateTime, DraftDateTime, ResultedDateTime, Ordering Physician, TechnologistAssigned1, TechnologistAssigned2, TechnologistAssigned3, TechnologistAssigned4, and RadiologistAssigned. FIGS. 4a-4d show an example of a complete set of fields within the Master Exam Table (MET) stored in the facility database 105. This is also referred to as the database schema.

The DI modality devices may transmit image series information, such as the start and end time of the series, using a standard imaging system protocol, such as DICOM. This is used to transmit an image series to the PACS, but such a message may also be captured and interpreted by the facility IMAP 104. A technique known as port mirroring may be employed to listen on the network to capture all the DICOM information being sent to the PACS archive. Port mirroring refers to the duplication of an Internet Protocol (IP) address in a network switch to send the same data to two different devices at the end of a single but duplicated IP address, which ensures network traffic is not increased. It ensures that the facility IMAP 104 receives all the DICOM information being sent to the archive.

The collected DICOM information that is inserted into the database includes information such as DICOM_AETitle, DICOM_StudyDateTime, and DICOM_LastImageDateTime.

DICOM and HL7 are two different international standards that are not interoperable because the objectives and functions of the data being shared are for two different purposes. The objective of HL7 data is to pass patient demographics around the healthcare enterprise with the prime function being the tracking of patient Admission, Discharge and Transfer (ADT). HL7 broadcasts all messages across the network, permitting any device the opportunity to listen to the message. There is no confirmation that all information has been received and few if any fields are required to be filled in. In contrast, the objective of the DICOM file standard is to transfer patient image data between key devices within the Diagnostic Imaging department, and there is a series of DICOM messages to confirm that a patient study has been sent and that all data has been received. DICOM, unlike HL7, uses a point-to-point communication protocol to confirm it is speaking with the equipment it is programmed to share patient studies with. An initial handshake between devices confirms authentication of devices and is repeated at other times during the transfer of data, thus adding additional time for the transfer of data. Due to the differences in objectives and protocols for sharing information, these two international standards are not interoperable and, as a result, have left a void for years in the development of hybrid databases, which the imaging facility device information system 110 fills.

The facility IMAP 104 receives image series information transmitted by the DI modality devices and patient information broadcast by the RIS 101. The image series information includes the accession number which is used to match up patient information with image series information. The facility IMAP 104 extracts portions of this information to create patient records and stores them in the facility database 105. This includes all the information required to produce facility reports and exam record summaries (discussed later) for use by an imaging device regional information system.

The matching of patient HL7 data with the DICOM study data is achieved via the following method. Orders for patient exams are generated and entered into the RIS through a number of different methods. For example, each area of the hospital may have access to the hospital scheduling function within the HIS. A patient may be scheduled for a CT of the head. The order (requisition) for the study will sit in a holding area until the night before the study is to be completed. At midnight all the orders may be transferred to the RIS. Alternatively, a patient can walk into the DI department with an imaging request in paper form from a referring doctor and hand the paper to the clerical staff at the front desk. An order is then typed into the RIS for a patient study. In either case, once the order is received the RIS assigns an accession number for the study request. During the generation of the order within the RIS, the RIS assigns an accession number to the specific imaging study request and matches the patient's demographics to the accession number and the study code for that imaging study request. This information is then broadcast on the network and if, for example, the imaging study is for a CT Head, the CT device will pick this data up and, using a DICOM work list, create a record indicating that the patient is to have a CT Head study today, and populate the DICOM header with the patient's demographics, patient ID number, accession number, study type and specific study code. In interpreting this data the CT device may make errors in the populating of the DICOM header, and, as a result, this may create a "Broken Study" as the information in the RIS is different than in the DICOM file. The "Broken Study" is identified when the PACS archive checks the DICOM file information against the information as received from the RIS and it is found to be different. The PACS system administrator is then required to go into either the RIS or PACS archive and make the appropriate corrections. In the case when the data is transferred correctly, the facility IMAP 104 takes in data from the HL7 messages first and starts a new record in the database. When the first DICOM data is transferred to the PACS archive, the facility IMAP 104 then compares the patient demographics and accession number and patient ID number to confirm it is the same person as received before. Once this is confirmed the facility IMAP 104 will update the record with the incremental data received from the DICOM file header messages and then execute calculations to fill in other fields within the database. In the case where the patient demographics or identification do not match for one of many different reasons, the facility IMAP 104 then considers this to be a Broken Study and will isolate the data and report the studies that are considered to be broken, which may be done in a daily report and electronic dashboard. Users of the RIS, PACS, and modality can then check this list and make appropriate corrections in the HL7 records or DICOM Header Records and thus repair the study. When this has been completed and the data are re-broadcast or sent, the facility IMAP 104 will see the changes and will update the original record with the new correct information to confirm it is not broken and confirm it has the most recent correct data.

Figure 3:
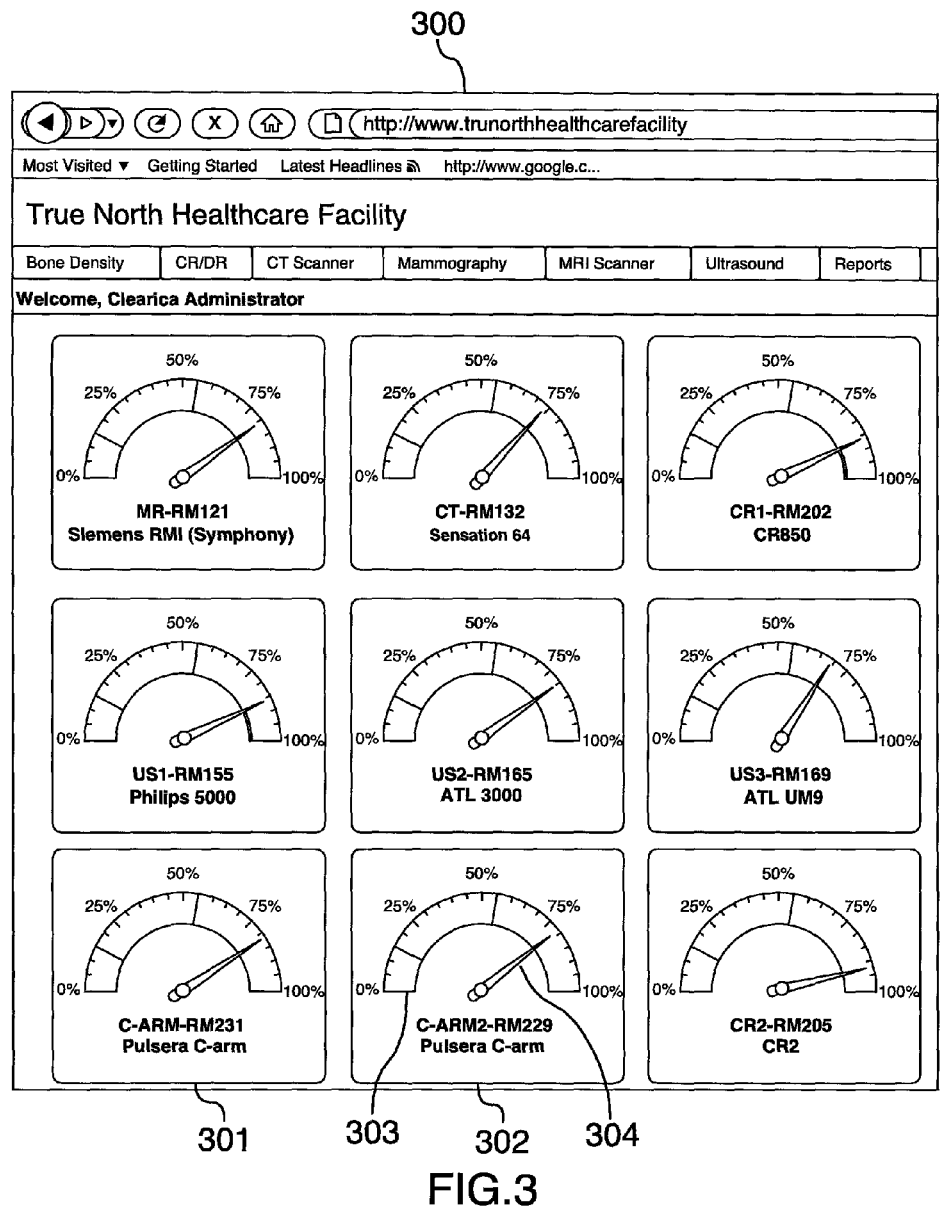
FIG. 3 is an example of a modality temporal utilization report.

FIG. 3 shows an example of one type of facility report, which is a modality temporal utilization report, displayed in the browser window 300 of an authorized facility user 109 on the facility local network 107. The report displayed in the browser window 300 shows the temporal utilization of a number of DI modality devices in the form of a digital dashboard, with the temporal utilization expressed as percentages. For example items 301 and 302 show the temporal utilization of one radio fluoroscope (RF) each, using a color coded scale 303 showing the temporal utilization and an indicator 304 showing the current utilization rate. For example, the current temporal utilization rate of device C-ARM2-RM229 is shown in item 302 to be approximately 79%. This may be the temporal utilization rate for the current day, or for some other time period specified by the authorized facility user 109 who requested this facility report. It may be computed by calculating the total time for which the DI modality device was used during that time period and dividing it by the duration of the time period. Other statistics may also be optionally reported, such as patient wait times, number of exams booked, in progress, completed, to be reported and reported in a given time period, and total workload units (actual, standard, or hospital specific standard) in a given time period. A time period might be, for example, the last hour, the current day, the previous day, the current or previous shift, or the year to date. The temporal utilization of a DI modality device may be calculated using the actual, CIHI guideline, or hospital specific workload units.

Figure 6:
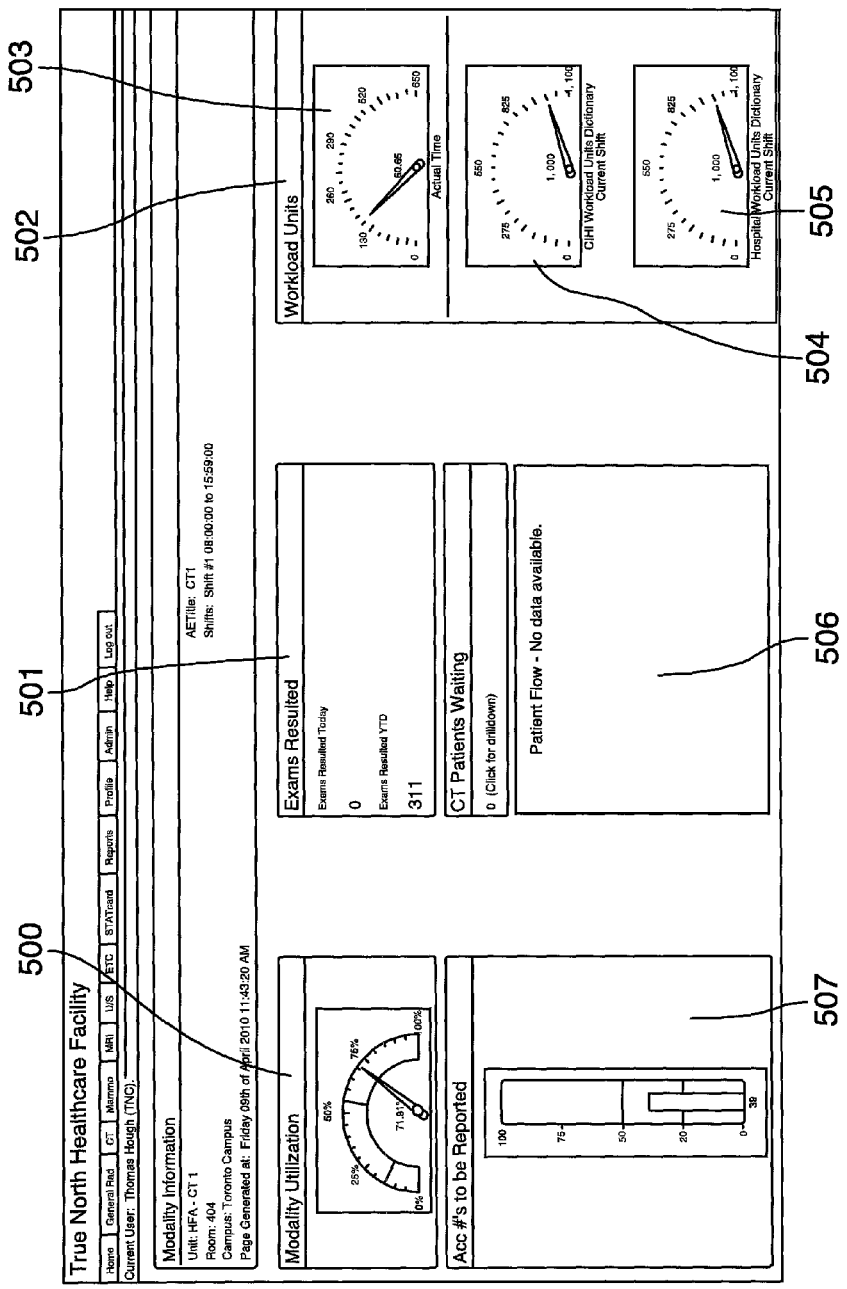
FIG. 6 is a drill-down report that may be displayed when a user clicks on the report shown in FIG. 3.

The report shown in FIG. 6 is a drill down report displayed when a user clicks on the report shown in FIG. 3. This is a temporal report showing additional information on the utilization for a specific modality, in this case CT. The Modality Utilization 500 is the same display as seen repeatedly in FIG. 3. This gauge represents, as a percentage, the amount of time the unit has been busy capturing images since the start of the work shift of image capture. To the right is Exams Resulted 501, which breaks down into two numbers: exams resulted on the day the report is generated and exams resulted year to date for this specific modality. To the right of this key performance indicator are three gauges entitled Workload Units 502. The top gauge 503 is the actual time in minutes the modality has been busy capturing images since the start of the work shift. The gauge 504 below is the total number of work load units for the case mix the modality has done on the day the report is generated for the current shift as per the CIHI guidelines. The final gauge 505 is the total number of workload units for the case mix the modality had done on the day the report is generated for the current shift as per the hospital's dictionary for studies. In many cases these two gauges 504, 505 will appear to be very close in number. To the left of these gauges on the bottom row is a Patient Waiting gauge 506. This displays how many patients are in the waiting room waiting for that modality, the number of patients that are in the exam room and having the study completed, and the number of patient's studies completed by that specific modality today. Double clicking on any of these three coloured areas will pop-up a list of the specific patient names and demographics relevant information to the study. The final gauge 507 is the accession numbers to be reported. This is a thermometer gauge indicating the number of patient studies the radiologists need to report for this modality device. When a patient is taken off this list it is added to the Exams resulted today and Exams Resulted YTD gauge 501.

The above describes the digital real-time dashboard displays within the facility IMAP 104. Numerous other reports are available for other types of operational and statistical analysis.

The facility reports are produced using the patient records in the facility database 105. The content of the patent records is tailored to provide all the information required to produce those reports, but exclude unnecessary information, such as diagnostic image data.

The imaging facility device information system 110 can be sold as a Software as a Service (SaaS) model, which includes all software, software updates, software upgrades, software service agreements, schedule of benefits updates, hospital dictionary, CIHI dictionary updates and hardware refreshes. Clients may e-mail, call in, or iChat with customer service personnel. Customer support personnel may remotely log-on to support the client's needs, diagnose reported problems and download fixes or call for hardware vendors to come and replace any defective parts.

Figure 2:
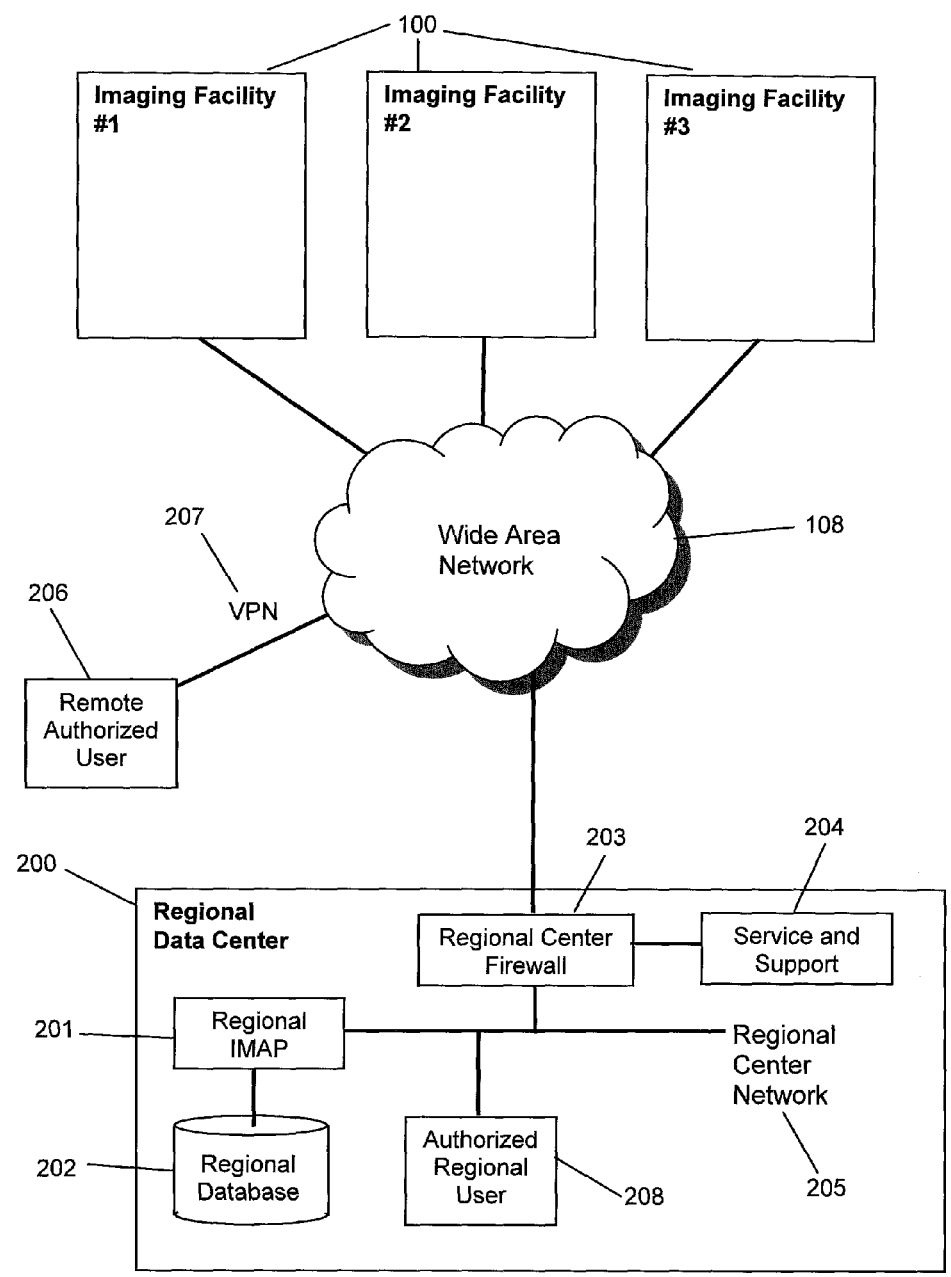
FIG. 2 is a diagram showing multiple imaging facilities and a regional data center.

In another embodiment, as shown in FIG. 2, which may be referred to as an imaging device regional information system, the system may comprise two or more imaging facility device information systems 110, located at geographically separated imaging facilities 100, and a regional IMAP 201, which is connected to and maintains a regional database 202. The regional IMAP 201 and regional database 202 may be located at a regional data center 200 having a regional center network 205 that connects the regional IMAP 201 to the wide area network 108 via a regional center firewall 203. A service and support 204 system may also be connected to the regional center firewall 203.

The regional IMAP 201 receives facility-independent exam record summaries from each facility IMAP 104. The exam record summaries are designed to exclude data that is not necessary for the production of regional reports, such as personal health information (PHI) of patients, such as their names and addresses. PHI is generally subject to various stringent privacy laws and policies and generally may not be disclosed other than to specifically authorized personnel. An authorized facility user 109 or remote authorized user 206 who has authorization to see PHI for a specific imaging facility 100 may be able to request that the facility IMAP 104 generate facility reports that include PHI.

The facility-independent exam record summaries may be sent periodically, such as once per day, or alternatively may be sent more frequently to provide real-time, or near real-time, status information to the regional IMAP 201 to allow it to produce regional reports that are up to date to the time at which they are requested. An authorized regional user 208 may be able to specify via a menu a temporal basis for comparing imaging facilities 100 with each other.

An example of an exam record summary is shown in FIG. 5, which summarizes the utilization of the ultrasound modality device (US1) at one hospital or imaging facility 100.

The facility IMAPs 104 create the exam record summaries from the information stored in the facility databases 105. Since each imaging facility 100 may use its own customized exam dictionary, the procedure codes used in each facility are not directly comparable. Each facility IMAP 104 makes the exam record summaries facility-independent through the use of a unique standardized dictionary, referred to the Gold Code. The Gold Code includes reimbursement and workload unit codes and is mapped against each hospital's own exam dictionary. Because it is mapped to each imaging facility's exam dictionary, it standardizes the imaging facility's exam codes to a common mapping definition which allows an apple-to-apple comparison of productivity in terms of Workload Units, Exam Counts, and Technical Fee Revenues.

A Gold Code dictionary of DI exam procedures is used to map codes from different imaging facilities to a uniform set of codes to permit meaningful inter-facility comparisons. Each exam procedure listing contains the appropriate workload unit code mappings of payment plans for technical and professional reimbursement codes and fees. Each individual imaging facility's DI Exam dictionary is mapped against the Gold Code dictionary using the exam dictionary. Where there are differences found between a facility's exam dictionary and the gold code dictionary, these are noted in a code log of differences. When a facility's numbers of procedures are compared against another facility's numbers of procedures the "Gold Code" is applied to calculate the exam (study) volumes, workload units, the technical fees and professional fees, for example. This results in a standard basis of comparison.

The regional IMAP 201 then uses the facility-independent exam record summaries to produce regional reports for inter-hospital comparison in response to requests from authorized regional users 208 or remote authorized users 206. These reports may show, for example, a user-selected number of imaging facilities side by side, modality by modality, on the same chart to facilitate comparisons. Each imaging facility's identity may be masked and anonymized except for the imaging facility 100 associated with the user who is requesting the report.

Figure 7:
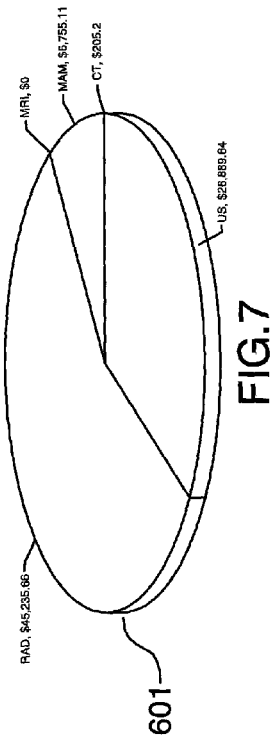
FIG. 7 is an example of a regional report.

FIG. 7 shows an example of a portion of a regional report showing three different sites that compares their revenue by modality type and volume of studies for the current month. Below the table that displays the numbers for each hospital are pie charts (only one is shown in FIG. 7). The first chart 601 is the revenue pie chart for the first hospital. Other reports exist and can be configured to display whatever comparison users select, for example, by dragging and dropping database elements, to compare them in pivot tables and/or other types of charts over various time periods as requested.

Remote authorized users 206 may be able to request the generation of facility reports and regional reports. A remote authorized user 206 may have authorization to request facility reports from one or more facility IMAPs 104 via a web browser in the same manner that an authorized facility user 109 may. The facility IMAP 104 may act as a web server for this purpose and allow the user to obtain reports by a secure mechanism, such as a VPN 207 or via an authenticated HTTPS interface. Similarly the regional IMAP 201 may act as a web server to allow a remote authorized user 206 or an authorized regional user 208 to request and obtain regional reports.

A facility report, such as a modality temporal utilization report, may be used by administrative staff of the imaging facility 100 to assess the need for changes to operations of the imaging facility 100. For example, where such a report indicates that a particular DI modality device is used less than a certain amount, i.e. is under-utilized, corrective action may be required. For example, from prior experience, it may be known that a device of a certain modality should be used at least 60% of the time in the absence of problems such as too few patients requiring imaging series using that modality device and technical problems with the device, or insufficient number of imaging facility staff attending the device. If a modality temporal utilization report shows that a particular device has a temporal utilization rate below 60% it may indicate that one of these problems exists. In the absence of a lack of patients requiring image series using that modality and technical problems with the device, this may indicate that the imaging facility has an insufficient number of staff members capable of operating and available to operate, or attend, that DI modality device. Thereby it may be determined that the number of attending imaging facility staff needs to be increased, either by training additional staff to operate the device or by adding additional trained staff members, and the imaging facility 100 administrative staff may take such action. As another example, it may be determined that the low temporal utilization of the device is due to some intermittent technical problem, which may then result in technicians being called in to investigate and repair the device.

In the instance of a hospital not meeting a benchmarked target for workload units when compared against peer hospitals, the daily volume of workload units may fall short of the required targets due to one of many reasons. This may be because, for example, the study code dictionary does not have correct workload units assigned for each study code or the staff is not including additional workload units when doing an extra option on the study. For example, when an Ultrasound study is being completed, the sonographer may decide to add a Doppler flow to the study. If the sonographer neglects to modify the study code to include this, the associated workload units are not included, resulting in a shortfall for the daily total. Being able to see dynamically during the day how the unit and the department is tracking toward the required workload units along with retraining of staff may ensure users do not leave workload units uncounted and provide a realistic representation of the true amount of work completed by the hospital.

The ability for inter-hospital benchmarking on a true apple-to-apple basis enables authorized users to compare like-sized hospitals to see where operational excellence is being achieved and where remedial assistance is required. For example, Hospital A may be performing at a higher level than any other hospital in the area of CT utilization, but hospital A may be in the bottom quartile in Ultrasound utilization. Wait times may be excessively long in hospital A for ultrasound due to their poor schedule management. The Local Healthcare Integrated Network (LHIN) may review this and decide to shift two ultrasound units from hospital A to hospital C, which is nearby and operating in the top quartile of peer Ultrasound departments. This may be done because the cost per study in hospital C is less than performing the same exam in hospital A, and physicians may be instructed to direct their referrals to hospital C. In response to this action, the LHIN may adjust the funding to hospital A by increasing funding for the global budget as a result of the CT utilization and reducing the funding as a result of the Ultrasound utilization. By shifting the physical assets to hospital C which can perform the exams for the least cost, the funding for hospital C can be adjusted for the increased volume, but not by the amount saved by taking it away from hospital A, resulting in a overall lower cost to provide healthcare within the LHIN.

The computer-based processors described herein may be run on a single computer system comprising a processor, network interface for accessing the local area network, storage means such as semiconductor memories and hard disk drives, and software running on the processor to cause it to perform the described functions. Such an application may alternatively be run on a distributed system including multiple processors communicating via a communication network. Such a system may alternatively be a purpose-built processor, or network of processors, comprising computer hardware designed to perform the functions described herein. In all cases, each embodiment of these systems and subsystems is a particular machine that performs the described functions in the manner described herein as they would be understood by a skilled person.

It will be appreciated that the above description relates to the described embodiments by way of example only. Many variations on the system and method for delivering the invention without departing from the spirit of same will be clear to those knowledgeable in the field, and such variations are within the scope of the invention as described and claimed, whether or not expressly described.

What is claimed is:

1. An imaging facility device information system for use in an imaging facility having a radiology information system, a picture archiving and communication system (PACS) and a plurality of diagnostic imaging modality devices, all of the foregoing connected to a local network, the facility information system comprising:
   a. a facility imaging modality analysis processor, the facility imaging modality analysis processor comprising a computer processor and being connected to the local network and configured to receive patient information from the radiology information system and configured to capture and interpret image series information of patients from the diagnostic imaging modality devices when the diagnostic imaging modality devices transfer image series to the PACS; and
   b. a facility database in electronic communication with the facility imaging modality analysis processor;
   wherein the facility imaging modality analysis processor combines the image series information of each patient with the patient information for the corresponding patient into patient records in the facility database,
   and wherein when the image series information is captured by the facility imaging modality analysis processor, an associated binary image from the image series is not captured,
   and wherein the facility imaging modality analysis processor produces facility reports from the patient records, the facility reports containing an analysis of the temporal utilization of the diagnostic imaging modality devices,
   and wherein when the facility imaging modality analysis processor produces facility reports, the facility imaging modality analysis processor analyzes both temporal data in the image series information that was obtained from header data from the image series transmitted using a standard medical imaging system protocol, and patient information to determine the percentage of time the imaging modality devices were utilized during a particular period,
   and wherein the facility imaging modality analysis processor queries the PACS to identify changes made to the image series information and the facility imaging modality analysis processor updates the facility database to reflect changes that are identified.

2. The image facility device information system of claim 1 wherein the facility imaging modality analysis processor receives image series information using a standard imaging system protocol and receives patient information using a standard radiology information system protocol.

3. The image facility device information system of claim 2 wherein the standard radiology information system protocol is the Health Level 7 (HL7) international standard for messaging and the standard imaging system protocol is the Digital Imaging and Communications in Medicine (DICOM) international standard.

4. The image facility device information system of claim 1 wherein the facility imaging modality analysis processor allows authorized facility users to request facility reports using a web browser.

5. The image facility device information system of claim 2 wherein the facility imaging modality analysis processor allows authorized facility users to request facility reports using a web browser.

6. The image facility device information system of claim 3 wherein the facility imaging modality analysis processor allows authorized facility users to request facility reports using a web browser.

7. An imaging device regional information system comprising
   a. at least two imaging facility device information systems of claim 1 connected to a wide area network, and
   b. a regional imaging modality analysis processor connected to the wide area network,
   wherein the imaging facility device information systems further produce facility-independent exam record summaries that are transmitted to the regional imaging modality analysis processor and wherein the regional imaging modality analysis processor produces regional reports from the facility-independent exam record summaries comparing the temporal utilization of the diagnostic imaging modality devices between imaging facilities.

8. The imaging device regional information system of claim 7 wherein the regional imaging modality analysis processor allows authorized regional users to request regional reports using a web browser.

9. The imaging device regional information system of claim 7 wherein the imaging facility device information systems update the patient records in real-time and send the exam record summaries to the regional imaging modality analysis processor in real-time, and the regional imaging modality analysis processor then produces regional reports in real-time or near real-time.

10. The imaging device regional information system of claim 8 wherein the imaging facility device information systems update the patient records in real-time and send the exam record summaries to the regional imaging modality analysis processor in real-time, and the regional imaging modality analysis processor then produces regional reports in real-time or near real-time.

11. A method for analyzing temporal utilization of diagnostic imaging modality devices performed by a computer processor running software, the method comprising the steps of:
   a. receiving, by the computer processor, patient information from a radiology information system;
   b. capturing and interpreting, by the computer processor, image series information of patients from the diagnostic imaging modality devices when the diagnostic imaging modality devices transfer image series to a picture archiving and communication system (PACS), wherein when the image series information is captured by the computer processor, an associated binary image from the image series is not captured;
   c. combining, by the computer processor, image series information of each patient with patient information for the patient into patient records;
   d. producing, by the computer processor, facility reports from the patient records, the facility reports containing an analysis of the temporal utilization of the diagnostic imaging modality devices, wherein when the computer processor produces the facility reports, the computer processor analyzes both temporal data in the image series information that was obtained from header data from the image series transmitted using a standard medical imaging system protocol, and patient information to determine the percentage of time the imaging modality devices were utilized during a particular period;

e. querying, by the computer processor, a picture archiving and communication system to identify changes made to the image series information; and f. updating, by the computer processor, the facility database to reflect changes that are identified.

12. The method of claim 11 wherein the image series information is received using a standard imaging system protocol and the patient information is received using a standard radiology information system protocol.

13. The method of claim 12 wherein the standard radiology information system protocol is the Health Level 7 (HL7) international standard for messaging and the standard imaging system protocol is the Digital Imaging and Communications in Medicine (DICOM) international standard.

14. The method of claim 11 further comprising the steps of analyzing the facility reports to identify an under-utilized diagnostic imaging modality device and increasing the number of imaging facility staff attending that diagnostic imaging modality device so that the temporal utilization of the under-utilized diagnostic imaging modality device is increased.

15. The method of claim 12 further comprising the steps of analyzing the facility reports to identify an under-utilized diagnostic imaging modality device and increasing the number of imaging facility staff attending that diagnostic imaging modality device so that the temporal utilization of the under-utilized diagnostic imaging modality device is increased.

16. The method of claim 13 further comprising the steps of analyzing the facility reports to identify an under-utilized diagnostic imaging modality device and increasing the number of imaging facility staff attending that diagnostic imaging modality device so that the temporal utilization of the under-utilized diagnostic imaging modality device is increased.

17. The method of claim 11, further comprising the steps of analyzing the facility reports to determine that a diagnostic imaging modality device has a technical problem and having technicians repair the diagnostic imaging modality device.

18. The method of claim 12, further comprising the steps of analyzing the facility reports to determine that a diagnostic imaging modality device has a technical problem and having technicians repair the diagnostic imaging modality device.

19. The method of claim 13, further comprising the steps of analyzing the facility reports to determine that a diagnostic imaging modality device has a technical problem and having technicians repair the diagnostic imaging modality device.

* * * * *